United States Patent
Selvin et al.

(10) Patent No.: US 9,229,006 B2
(45) Date of Patent: Jan. 5, 2016

(54) SMALL WATER-SOLUBLE QUANTUM DOTS

(71) Applicant: THE BOARD OF TRUSTEES OF THE UNIVERSITY OF ILLINOIS, Urbana, IL (US)

(72) Inventors: Paul R Selvin, Urbana, IL (US); Pinghua Ge, Urbana, IL (US)

(73) Assignee: Board of Trustees of the University of Illinois, Urbana, IL (US)

(*) Notice: Subject to any disclaimer, the term of this patent is extended or adjusted under 35 U.S.C. 154(b) by 169 days.

(21) Appl. No.: 14/184,558

(22) Filed: Feb. 19, 2014

(65) Prior Publication Data
US 2015/0236220 A1 Aug. 20, 2015

(51) Int. Cl.
| | |
|---|---|
| G01N 33/58 | (2006.01) |
| H01L 33/50 | (2010.01) |
| H01L 33/28 | (2010.01) |
| H01L 33/06 | (2010.01) |
| C09K 11/08 | (2006.01) |
| C09K 11/56 | (2006.01) |
| C09K 11/00 | (2006.01) |

(52) U.S. Cl.
CPC ............ *G01N 33/587* (2013.01); *C09K 11/00* (2013.01); *C09K 11/0811* (2013.01); *C09K 11/565* (2013.01); *G01N 33/588* (2013.01); *Y10S 977/74* (2013.01); *Y10S 977/774* (2013.01); *Y10S 977/883* (2013.01); *Y10S 977/892* (2013.01)

(58) Field of Classification Search
CPC ............ Y10S 977/774; Y10S 977/883; Y10S 977/74; Y10S 977/892; G01N 33/588; C09K 11/565; C09K 11/0811
See application file for complete search history.

(56) References Cited

U.S. PATENT DOCUMENTS

| | | | | |
|---|---|---|---|---|
| 7,041,371 | B2 * | 5/2006 | Ogura | ............ C30B 7/00 252/301.4 R |
| 2011/0165647 | A1 * | 7/2011 | Fernig | ............ B82Y 15/00 435/188 |

* cited by examiner

*Primary Examiner* — Carol M Koslow
(74) *Attorney, Agent, or Firm* — Richard Aron Osman

(57) ABSTRACT

Water-soluble, stable fluorescent PEGylated alkanethiol-coated quantum dots are made by contacting quantum dots with PEGylated alkanethiol in a non-oxidative, water-immiscible organic reaction solvent under a non-oxidative gas, wherein the reaction solvent is in contact with an aqueous phase, at elevated temperature and time sufficient to coat the dots with the PEGylated alkanethiol, wherein resultant water-soluble, stable fluorescent PEGylated alkanethiol-coated dots enter the aqueous phase.

20 Claims, 1 Drawing Sheet

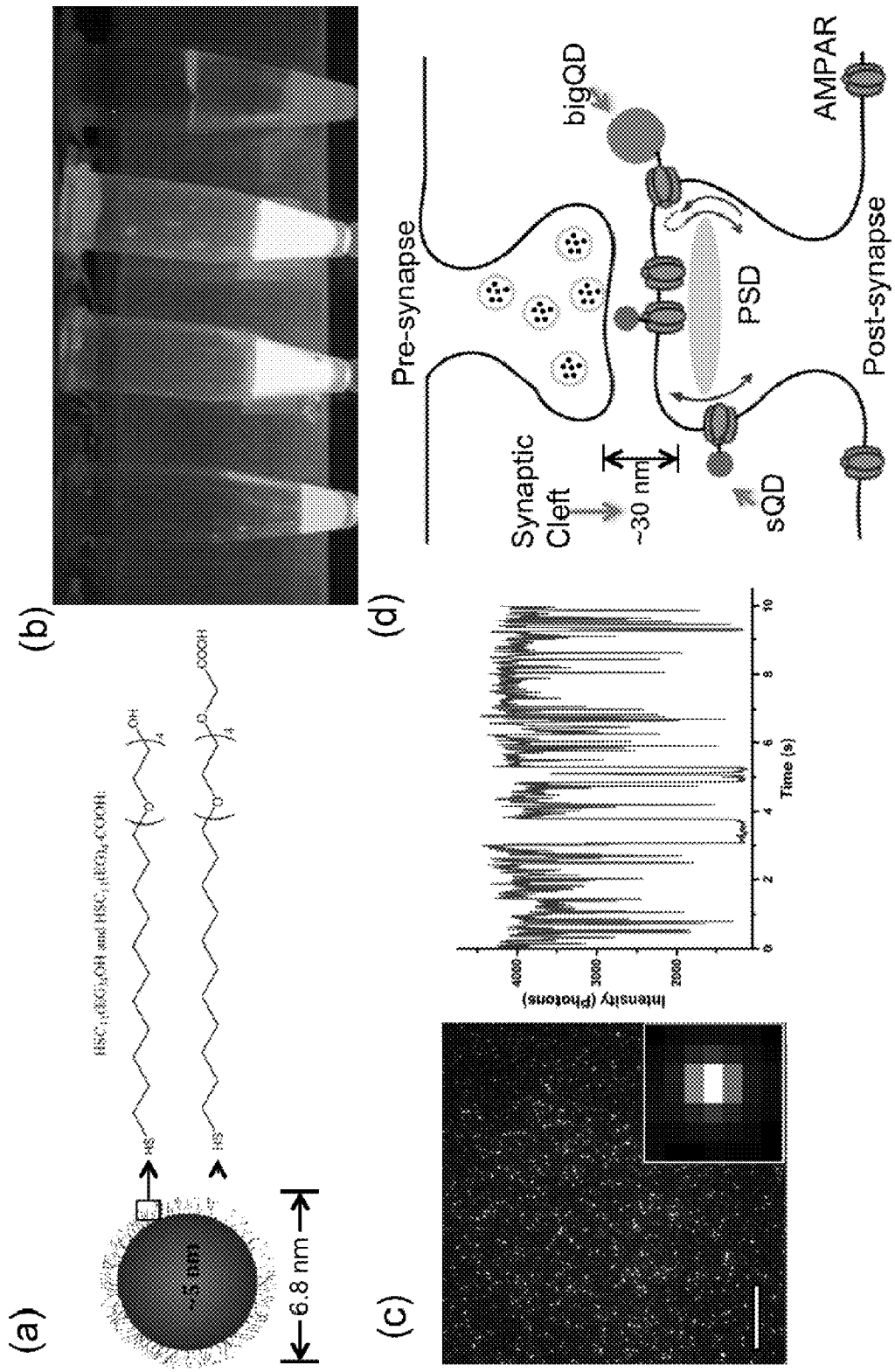

SMALL WATER-SOLUBLE QUANTUM DOTS

STATEMENT RE GOVERNMENT RIGHTS

This invention was made with government support under National Institutes of Health grant GM086214/MIT Sub Award 0571002579, and National Science Foundation grants MCB1216342, DBI 1243568 and PHY0822613. The government has certain rights in the invention.

INTRODUCTION

Quantum dots (QDs), made of semiconductor nanocrystals, are highly advantageous in fluorescence applications due to their brightness and high photo-stability[1]. However, their large diameters, typically around 15-35 nm, make them hard to access crowded cellular environments[2] (also, Sperling, R. A. et al. Size Determination of (Bio)conjugated Water-Soluble Colloidal Nanoparticles: A Comparison of Different Techniques. *J. Phys. Chem. C* 111, 11552-59, 2007). There have been attempts to make smaller QDs, generally with diameters on the order of 10 nm[3-5]. However, small quantum dots usually suffer either from chemical instability or poor labeling specificity[2].

Achieving specific labeling with small QDs is particularly challenging, especially when labeling the neuronal synapses, a ~30 nm spacing involved in neuronal communication and filled with sticky proteins. The commercially available QDs (bQDs), such as the ones from Invitrogen, have had success in labeling neurons, although a majority of bQDs (typically ~70%-90%) label extra-synaptically, rather than intra-synaptically due to their large sizes[4,6]. The difficulty of commercial QDs in accessing synaptic clefts is particularly problematic when studying AMPA receptors, which have a tendency to diffuse in and out of the synapse in response to memory formation[7,8]. Therefore, QDs with smaller sizes are desirable.

The QD is typically made of a core, which is then coated with a passivating layer to maintain the fluorescence even in the presence of water, and then has a number of biomolecular-reactive entities. The large size of the QD primarily results from its passivating coating, and secondarily, from the attachment of biomolecules. The quantum dot core, often made out of Cadmium Selenide (CdSe) with a ZnS shell, is typically 2-7 nm in diameter; the size of the core is precisely controlled to give the desired wavelength of emission. This CdSe/ZnS structure is hydrophobic and quenched by water. To protect the quantum dots cores from quenching and make them water-soluble, carefully selected groups of chemicals are used to coat the surface of the core/shell structure. Commercial QDs are usually coated with large polymers, which contribute much to their size. Multiple active sites for attaching functional groups also increase the overall QD size. Other coating methods have been developed to reduce the size of the quantum dots[3,9-11]. Howarth et al. reported the use of dihydrolipoic acid (DHLA)-PEG derivatives for coating CdSe/ZnCdS QDs which reduced the size of QDs to 11.1 nm and are stable at 37° C. for more than 4 hours[4]. The reduced-sized QDs were reported to have better accessibility to the synaptic cleft compared to bQDs. Zhan et al, have reported a new method of making small quantum dots, although they have not tested them on neurons[5]. Nishimura et al. (Biocompatible fluorescent silicon nanocrystals for single-molecule tracking and fluorescence imaging. *J Cell Biol* 202(6), 967-983, 2013) have made some 4 nm silicon nanocrystals which do not blink or photobleach, although they require UV excitation, have relatively low extinction coefficients compared to quantum dots, and have a broad (~100 nm) emission spectra.

Here we report a simple and robust coating method for CdSe/ZnS core-shell QDs with self-assembled monolayer (SAM)[12-14] of ligands. For these coated QDs, we sometimes distinguish the outer coating from the inner core, though in that context, the inner core itself typically comprises a core and a shell; however, which "core" is referenced will be clear from context.

SUMMARY OF THE INVENTION

The invention provides compositions comprising water-soluble, stable fluorescent PEGylated alkanethiol-coated quantum dots, and related methods of making and use.

In one aspect the invention provides a composition comprising an organic phase comprising quantum dots and PEGylated alkanethiol, at elevated temperature (e.g. 40-80 C) and under a non-oxidative gas, in contact with an aqueous phase comprising water-soluble, stable fluorescent corresponding PEGylated alkanethiol-coated quantum dots.

In another aspect the invention provides methods of making water-soluble, stable fluorescent quantum dots, the method comprising: contacting quantum dots with PEGylated alkanethiol in a non-oxidative, water-immiscible organic reaction solvent under a non-oxidative gas, wherein the reaction solvent is in contact with an aqueous phase, at elevated (e.g. 40-80 C) temperature and time sufficient to coat the dots with the PEGylated alkanethiol, wherein resultant water-soluble, stable fluorescent PEGylated alkanethiol-coated dots enter the aqueous phase.

In particular embodiments:
- the incubation temperature is 50-70 C or about 60 C, and the time is 1-8 hours, or about 2 or 3 or 4 hours;
- the gas is or comprises an inert gas like nitrogen or a noble gas, like argon;
- the reaction solvent is or comprises toluene, chlorobenzene, or octane; and/or
- the aqueous phase tetraethylammonium hydroxide (20% wt) in water.

In other embodiments
- the dots comprise a nanocrystal metal core of CdSe, HgCdSe, CdTe, ZnTe, ZnS, CdS, InAs, etc.;
- the dots further comprise a shell of ZnS, CdS, CdSe, etc.; for example, CrystalPlex provides a ZnS core (different ratios) and a ZnS shell; and/or
- the coated dots have a diameter less than 10 or 8 nm.

In particular embodiments the PEGylated alkanethiol is in a mixture of the PEGylated alkanethiol and functionalized PEGylated alkanethiol, wherein the functionalized (e.g. carboxyl- or amine-PEGylated alkanethiol) component is preferably, about 50%, or less, or about 30, 20, 10, 5, 2.5 or 1%, compared with the hydroxyl component, and wherein the functionalized and non-functionalized components may be the same (corresponding) or different PEGylated alkanethiols, and in a more particular embodiment, the mixture is HSC11(EG)4-OH/HSC11(EG)4-COOH (2.5%).

The functionalized PEGylated alkanethiols provide a functional or reactive or activatable group, which may be further functionalized for particular applications; for example, a carboxyl or amine functional group may be readily coupled, using conventional chemistry, with a linker or affinity tag, like biotin or an antibody (or binding site thereof).

In particular embodiments, the method further comprises steps of:
- isolating the coated dots, e.g. with anion exchange chromatography;
- washing the aqueous phase containing the coated dots with a water-immiscible organic wash solvent (e.g. chloroform) and then isolating the coated dots, e.g. with anion exchange chromatography;
- isolating the coated dots and storing the isolated dots under refrigeration, preferably around 4 C, or at subzero (e.g. −10 or −20 C) temperature for days (e.g. at least 24 hrs, 3 days, or 10 days) or over a month; or isolating the coated dots and storing in a mixture comprising ethylene glycol (at least 20% or 50%).

In another aspect, the invention provides methods of using the subject isolated dots to label neurons, e.g. as exemplified herein.

The invention encompasses all combinations for particularly recited embodiments as though each combination had been separately and laboriously recited. For example, the invention includes the embodiment where wherein:

the elevated temperature is about 60 C and the time is about 4 hours;
the gas comprises inert gas that is nitrogen;
the reaction solvent comprises toluene; and
the aqueous phase comprises tetraethylammonium hydroxide (20% wt) in water.

And by further example, the invention includes the embodiment wherein:

the dots comprise a nanocrystal metal core of CdSe, HgCdSe, CdTe, ZnTe, or ZnS;
the dots further comprise a shell of ZnS or CdS; and
the coated dots have a diameter less than 10 nm.

In particular embodiments the —COOH component is minimized, to reduce non-specific labeling, e.g. the PEGylated alkanethiol is provided in a —OH/—COOH ratio of at least 50, 75, 90, 95, 97.5, or 99%. The quantum dots provide an intensely fluorescent object, which is easily bright enough to see at the single molecule level. It is also highly photostable, with fluorescence at the single-molecule level lasting for several minutes or several tens of minutes or hours). It also spontaneously blinks, which is desirable for making "super-resolution" measurements. Our manufacturing improvements include deoxygenation conditions and elevated temperature (about 60 C), when coupling the ligand. We also have stored the small qdot at subzero temperatures (e.g. about −20 C) and/or in the presence of ethylene glycol (e.g. about 50%-100%) to improve the shelf-life.

Since the coating ligand is small, for example, ~3.6 nm in length, and the ligand make a 30 degree angle with the QD core surface, adding the ligand effectively adds only about 2.3 nm in diameter to the QD core, resulting in small sized QDs. In addition, small QDs with a large number of —COOH carry higher negative charges. In the coating process, these highly negative-charged sQDs can be substantially eliminated by the anion exchange column chromatography. The remaining —COOH on the sQDs may be functionalized, e.g. coupled with streptavidin (SA). Therefore the total charge of sQDs is practically neutral.

Commercial QDs with SA have 4-10 streptavidin molecules per QD. In our example, the percentage of ligand HS—$(CH_2)_{11}$-$(EG)_4$-COOH is only about 2.5%, therefore, most of small QDs only have one or two streptavidin molecules, very few sQDs carry more than two SAs. Limiting the number of SAs per QD also helps control the small QD size. Limiting the number of SA per sQD also reduces biotin binding sites, which reduces the possibility of crossing linking receptors

BRIEF DESCRIPTION OF THE DRAWINGS

FIG. 1. Characterizations of stable small quantum dots (sQDs). (a) Schematic diagram of the stable sQD. Stable sQDs are coated with PEGylated alkanethiol ligands by self-assemble-monolayer. (b) Fluorescence of stable sQD 527, 615, 620 and 655 in phosphate buffer (PBS) under UV illumination. Stable sQDs are soluble and mono-dispersed in PBS. (c) Single molecule fluorescent image of sQD-620 nm-SA bound to biotin fixed on a coverglass. Fluorescent intensity of stable sQD-620 nm over time is shown at right. Blinking behavior is observed. (d) Schematic diagram of the synaptic region with AMPA receptors (AMPAR) labeled with sQDs and commercial QDs.

DETAILED DESCRIPTION OF SPECIFIC EMBODIMENTS OF THE INVENTION

By example we report that coating with a thin, but stable, ligand-layer over the usual CdSe/ZnS-QD cores, allows for compact probes, which provide, for example, substantially improved access to neuronal synapses. We use a self-assembled monolayer[10] of hydrophilic ligands with the structure HS—$(CH_2)_{11}$-$(EG)_4$-OH/COOH (EG: Ethylene glycol) (FIG. 1b). The undecanethiol termination provides a hydrophobic attachment to the nanoparticle surface that resists desorption, and unlike bulkier DHLA-based ligands, packs densely on the QD surface. The short $EG_4$ chain provides hydrophilicity for stable aqueous dispersion. A key parameter in the coating procedure is the use of elevated temperature without oxygen (e.g. 60° C., 4 hr, $N_2$) to drive replacement of the native hydrophobic ligands with a dense layer of the new ligands. The ligand monolayer makes them stable in water (>1 month) and brightly fluorescent (28% quantum yield). They are also resistant to non-specific binding to biomolecules, across a wide panel of QD crystal sizes (3.2-8 nm), sources (NN-labs, Invitrogen, and laboratory-made), and batches, yielding a broad spectrum of fluorescence wavelengths (FIG. 1c). For the sake of simplicity, we call them small QDs (sQDs).

Streptavidin (SA) was conjugated to the COOH-functionalized sQDs via a straightforward EDC coupling method. Individual sQDs were bound to biotin molecules on a PEGylated coverslip, and fluorescent blinking was observed (FIG. 1d). The average intensity was approximately ⅓ that of the bQDs. By only using a small number of COOH groups (2.5%) in the ligand layer, the rest being OH groups, nonspecific labeling is minimized and only a small number of bioaffinity molecules can attach to maintain a small particle size. Dynamic light scattering (DLS) measurements showed that the hydrodynamic diameter of the carboxylated sQD-620 was 6.8±0.2 nm and the size of SA-functionalized sQD-620 was 7.9±0.3 nm in diameter. The modest size-increase of 1.1 nm after functionalization indicates that the number of SAs on the surface of sQDs is limited, minimizing steric hindrance (FIG. 1a). These functionalized sQDs are stable for over one month under refrigeration, e.g. at 4° C.

Results

To synthesize water soluble sQDs, the CdSe/ZnS core/shell in organic solvent underwent coating exchange with the mixture of $(EG)_4$-alkanethiol and carboxyl-$(EG)_4$-alkanethiol:

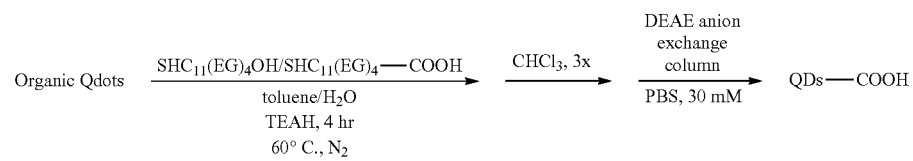

$HSC_{11}(EG)_4OH$ and $HSC_{11}(EG)_4$-COOH:

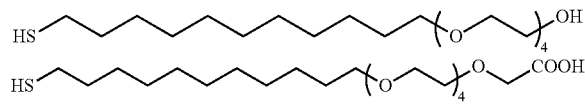

In brief, the organic CdSe/ZnS was mixed with $HSC_{11}(EG)_4$-OH (97.5%)/$HSC_{11}(EG)_4$-COOH (2.5%) in $H_2O$/toluene with tetraethylammonium hydroxide as base. The mixture was heated to 60° C. for 4 hour under nitrogen. During the process, the fluorescence of quantum dots transferred from the organic phase to aqueous phase. The mixture was washed with chloroform three times. The aqueous solution was then passed through a self-packed DEAE anion exchange column. The neutral QDs were primarily washed off with water first. The negatively-charged QDs were then washed off with 30 mM PBS to get the QD-COOH aqueous solution. The QD-COOH was further conjugated to streptavidin (SA) via EDC coupling method. Fernig et al. used the similar coating ligands but different coating exchange method to make water soluble sQDs[10]. The improved procedure reported here is necessary to successfully coat QD cores from different sources. The sources include cores from a variety of commercial sources, including N,N-Labs, from Invitrogen, and from laboratory-made sources.

The SAM of ligands provided a thin and stable coating over the sQDs, making it resistant to non-specific binding to biomolecules. The sQDs with a large number of carboxyl groups are highly negatively charged which are eliminated by the anion exchange column. The remaining carboxyl groups on the sQDs are coupled with SA, rendering sQDs with neutral charge. The sQDs are mono-dispersed in aqueous solution (PBS) (FIG. 1b).

Single molecule fluorescent imaging showed that individual sQDs specifically bound to biotin molecules on a PEGylated coverslip, and blinking was observed (FIG. 1c). The blinking showed the usual power law dependence, with the on brightness equal in intensity to that of the Invitrogen commercially available QDs. For 620 nm emitting sQD, the quantum yield is 28%. Dynamic light scattering (DLS) measurement shows that the hydrodynamic diameter of the carboxylated 620 nm emitting sQD is 6.8±0.2 nm and the size of SA functionalized sQD is 7.9±0.3 nm in diameter. The modest size-increase of 1.1 nm after functionalization indicates our sQDs have limited number of SAs on the surface. (Invitrogen QDs are reported to have 4-10 SA's.) With the significantly reduced size, an SA functionalized sQD will be much easier to get into a confined space, such as a synaptic cleft, than a commercial QD with multiple SAs (FIG. 1d). Stored at 4° C., the sQDs are stable for over 1 month.

A major concern for labeling neurons is non-specific interactions between sQDs and neurons, as well as between the sQDs and the substrate, particularly positively charged poly-L-lysine, which is used to adhere neurons onto the coverslip. Imaging showed AMPAR on cultured neurons labeled with high specificity using laboratory-made 527 nm emitting sQDs, i.e., only sQDs bound to AMPA receptors are present and free sQDs are essentially eliminated. Small QDs with other emission wavelengths also achieved high labeling specificity on neurons. Imaging was achieved by co-transfect neurons with fluorescent protein tagged Homer1 and GluR2-AP and BirA-ER. Homer1 is a postsynaptic marker concentrated in the postsynaptic density (PSD). Here it serves to locate the position of the synapses. GluR2 is a subunit of the AMPA receptor and AP is a 15 amino-acid tag at the extracellular domain on the GluR2 subunit[15]. BirA-ER biotinylates the AP tag intracellularly[15,16]. We labeled biotinylated AMPA receptors on the surface of transfected neurons with sQDs, and observed overlap between the Homer1 (dsRed channel) and the AMPA receptors (sQD channel). On untransfected neurons, we found minimum labeling of the sQDs. The labeling specificity is comparable to bQDs, which is important for receptor-tracking experiments.

We have observed non-specific bindings of imperfectly coated sQDs when labeling neurons, in which case either the ligand attachment of the sQD, or the SA attachments, were incomplete. We have also found that sQDs with highly negative charges have the tendency of binding non-specifically. Filtering out negatively charged sQDs therefore is important for specific labeling receptors on neurons.

We next tracked AMPA receptors labeled with sQDs and bQDs to investigate the difference in their binding and diffusion behavior. The wide range of emission wavelengths of small QDs makes it possible to co-label neurons with a number of fluorescent proteins as pre- or post-synaptic markers. In particular, we used photoactivable fluorescent proteins for super-resolution imaging, achieving 10-20 nm resolution in the x-y axis, and roughly two-fold worse in the z-dimension. Homer1 was used as a postsynaptic marker, labeled with mGeos17, which emits in the GFP channel when activated. AMPA receptors were labeled with sQDs emitting at 620 nm for single particle tracking. The emission of the mGeos and sQD can be detected separately because of their distinct emission wavelengths. We performed 3D single particle tracking of the AMPA receptor via Fluorescence Imagining with One Nanometer Accuracy (FIONA) (Yildiz, Science 27 Jun. 2003, 300 (5628) pp. 2061-2065) and 3D super-resolution imaging of Homer1 using photoactivated localization microscopy (PALM)18,19,20. The super-resolution imaging allows us to localize the post-synaptic region and the single particle tracking method reveals the diffusion behavior of AMPA receptors around synapses. By combining single particle tracking and PALM we can examine the sQD labeled receptor diffusing into synapses with high spatial resolution.

We observed very different diffusion behavior for the sQD-labeled AMPA receptors compared to bQD-labeled AMPA receptors. AMPA receptors labeled with Invitrogen bQDs diffuse fast along dendrites, mostly moving between synapses. We observed that the AMPA receptors labeled with bQDs had a fraction of 11.2% of the population immobilized (diffusion coefficient $D<0.01$ $\mu m^2/s$), 29.1% of the bQD-labeled receptors are slow diffusing ($0.01$ $\mu m^2/s<D<0.1$ $\mu m^2/s$), and the majority of bQD-labeled receptors (59.5%) are fast diffusing ($D>0.1$ $\mu m^2/s$). In contrast, the sQD-labeled primarily AMPA receptors at the synapse, with another section labeled specifically at some other points along the dendrites. Whether these other points are synapses that are not labeled with a fluorescent Homer1, or is due to some other causes, is not known. Regardless, at these points, AMPA receptors tend to diffuse slowly. Only a small fraction of them travel large distance along the dendrites. In particular, 37.4% of sQD-AMPA receptors are immobile, 58.7% show slow diffusion and only 3.9% were fast diffusing. Interestingly, it appears that AMPA receptors when in the synapse, primarily bind to a sub-section of the Homer1. This restricted binding, called nanodomains, has been seen by others (e.g. Nair et al. (2013). Super-resolution imaging reveals that AMPA receptors inside synapses are dynamically organized in nanodomains regulated by PSD95. *Journal of Neuroscience*, 33(32), 13204-13224; MacGillavry, et al. (2013). Nanoscale Scaffolding Domains within the Postsynaptic Density Concentrate Synaptic AMPA Receptors. *Neuron*, 78(4), 615-622), although due to the photostability of the sQDs, we can visualize it for many minutes, instead of a few seconds. Histogram of diffusion coefficients further demonstrate that the majority of commercial QD-labeled AMPA receptors undergo unconfined diffusion on dendrites, while majority of the sQD-labeled AMPA receptors are trapped or diffusing slowly.

To rule out the possibility that surface chemistry of sQD vs. the bQDs is responsible for the different diffusion behavior of AMPA receptors, as opposed to the QD's sizes, we performed experiments of tracking AMPA receptors expressed in HEK cells where there are no confined spaces as in synapses. In these experiments, we observed similar diffusion behavior between bQDs and sQDs. The majority of AMPA receptors diffuse with D greater than 0.1 $\mu m^2/s$ labeled either with bQDs (74.5%) or sQDs (61.6%). We therefore conclude that the reduced diffusion coefficients of sQD-labeled AMPA receptors result from the reduced QD size.

Our sQDs make it easier to label AMPA receptors in the synapse. The sQD-labeled AMPA receptors in the synapse move in a confined space resulting in higher population of slow diffusion than the commercial QD-labeled receptor. To demonstrate, we examined the traces of AMPA receptors with respect to the location of Homer1 and found that indeed 37.2% of the traces of sQDs co-localized with Homer1 compared to 10.1% in the case of bQDs. Our results are consistent with previous finding that there was a significant increased number of sQD (~11 nm) labeled AMPA receptors co-localized with synapses compared to the bQDs labeled ones[4]. The difference reported here is that our sQDs are smaller, chemically more stable, and available based upon diverse commercial sources.

Conclusion:

We disclose a simple and novel method for coating quantum dot cores, which are much smaller (e.g. 7.9±0.3 nm) than commercially-available quantum dots, and smaller and chemically more stable than the previous generation of sQDs[4]. The newly developed sQD achieved specific labeling on neuronal receptors and make the synapse more accessible to sQD-labeled neuronal receptor. Combined with super-resolution imaging, which can localize pre- and post-synaptic region, the dynamic biomolecules labeled with sQDs involved in neuron transmission can be investigated by single particle tracking. The application is not limited to neurons or even cells, but to any space, particularly a confined or crowed space where small fluorescent probes with tremendous photostability are advantageous.

Materials & Methods

Chemicals and Instruments

The 620 nm organic QD (CZ600) was purchased from NN-Labs (Fayetteville, Ark.). The 655 nm organic QD (Q21721MP) was purchased from Invitrogen. The 527 nm and 615 nm QDs are synthesized in Andrew Smith's lab at UIUC. The PEGylated alkanethiol and carboxyl PEGylated alkanethiol were purchased either from Sigma-Aldrich (674508-250MG) or from ProChimia Surfaces (TH001-m11-0.2, TH003-m11-0.1). Streptavidin was purchased from Prospec-Tany TechnoGene Ltd., Ness Ziona, Israel). EDC (1-(3-dimehylaminopropyl)-3-ethylcarbodiimide.HCl) was purchased from ProteoChem (Cheyenne, Wyo., c1100-3×10 mg). All other chemicals or solvents are purchased from Sigma-Aldrich unless indicated otherwise.

The absorption spectra were measured in a Perkin-Elmer bio10 spectrometer. The size and potential were measured in a Marvin Instrument Ltd, nano-ZS Zetasizer). The cell images were taken with lab-build microscopy.

Coating sQD

The organic CdSe/ZnS core/shell underwent coating exchange with a mixture of commercially available PEGylated alkanethiol and carboxyl PEGylated alkanethiol. In brief, the organic CdSe/ZnS (25 µL, 2 mg/mL) was mixed with $HSC_{11}(EG)_4$-OH (40 µL, 100 µM)/$HSC_{11}(EG)_4$-COOH (2.5%) (10 µL, 10 µM in $H_2O$, degassed, 400 µL)/toluene (400 µL) with tetraethylammonium hydroxide (20% wt in $H_2O$) as base. The mixture was heated to 60° C. for 4 hour under nitrogen. During the process, the fluorescence of quantum dots transferred from organic phase into aqueous phase. The mixture was washed with chloroform three times (400 µL, 200 µL, 200 µL). The aqueous solution was then passed through a self-packed DEAE anion exchange column (GE Healthcare, 17-0709-10). The possible neutral QDs were washed off with water first. The negatively charged QDs were washed off with 30 mM PBS to get the QD-COOH aqueous solution. The QD-COOH can be further conjugated to streptavidin (SA), GFP, DNA, etc. via EDC coupling method.

For a typical QD-SA conjugation, 150 µL of QD-COOH solution (400 nM) in sodium borate buffer (20 mM, pH 7.4) was mixed with 15 µL of streptavidin solution in sodium borate buffer (20 mM, pH 7.4). To the mixture, 3 µL of EDC solution (freshly prepared in sodium borate buffer (20 mM, pH 7.4), 10 mg/mL) was added. The reaction mixture was stirred at room temperature for 2 hours. The conjugation solution was filtered through a centrifugal filter unit (100 k cut-off, Amicon Ultra UFC510024), and washed minimum 5 times with sodium borate buffer (10 mM, pH 8.3). The QDs were redissolved in PBS buffer (20 mM, pH 7.2), and filtered through a centrifugal filter unit (0.2 um, Pall Life Sciences, ODM02C34). The QD-SA filtrate was collected and stored at 4° C.

Characterization of sQD:

Size Measurement:

Dynamic light scattering (DLS) is employed to measure the sizes of 620 nm small qdots. The measurements were carried out with concentrated samples (>100 nM), after filtering through an Antontop 10 (0.02 µm, Whatman GmbH, 6809-1102) syringe filter before measurements. Each trace to get autocorrelation was acquired for 15 s and each autocorrelation curve was taken from 15 times run and then the size of small qdots was obtained by averaging the 30 times measurements. The autocorrelation function was analyzed using Zetasizer software (Ver. 7.02, Malvern Instruments Ltd.).

| Size of sQD (nm) | sQD 527 (lab made) | sQD 526 (CrystalPlex) | sQD 620 (NN-labs) |
|---|---|---|---|
| —COOH | 8.98 ± 0.52 | 8.1 ± 0.6 | 6.8 ± 0.15 |
| -SA | 9.94 ± 0.67 | 11.91 ± 1.31 | 7.9 ± 0.3 |

Fluorescence Properties of the sQD:

The quantum yield of sQD was measured by a spectrometer. The quantum yield for the core of sQD 620 in organic solvent before surface coating is ~50%. After coating and coupling to streptavidin, the quantum yield of the sQD 620 is 0.28. As a direct comparison for the brightness of commercial QDs and sQDs, we compared the single molecule fluorescent intensity of Invitrogen QD 655 and sQD 655 under the same illumination condition, and found the average intensity of sQD 655 is 56% of that of the Invitrogen QD 655. Therefore, with same core and same imaging condition, the brightness of sQD is about half as bright as commercial QDs.

Cell Culture and Labeling

HEK Culture:

HEK 293 cells (from ATCC) were grown in DMEM media supplemented with 10% FBS, 2 mM of L-Glutamine, and 100 units/ml of penicillin and 100 units/ml of streptomycin. Cells were transfected using Lippofectamine 2000. After about 6 hours of transfection, media were replaced with fresh media with 10 uM of biotin overnight and imaged the next day. Before imaging, cell were incubated with 2 ml of optimum, 1 mg/ml BSA and 1 mg/ml casein for 1 h at 37 C, 5% CO2. Wash 1× with DPBS, and incubated in imaging buffer (DPBS, 1 mg/ml BSA and 1 mg/ml casein, and 0.5 nM of QD605 Invitrogen/2 nM of sQD615) for 10 min at room temperature. Cells were washed 3× with PBS and imaged.

Neuron Culture:

Primary cortex and hippocampal cultures were prepared from E18-19 rats according to university guidelines. Neurons were dissociated in 3 mg/ml protease and plated on 18 mm coverslips coated with 1 mg/ml poly-L-Lysine. Neurons are cultured in 37 C, 5% $CO_2$ in neurobasal media with B-27 supplement, 2 uM glutmax and 50 unit/ml penicillin and 50 unit/ml streptomycin. On DIV11-13, neurons are co-transfected with Homer1-mGeos (0.4 μg/coverslip) with Glur2-AP (0.4 μg/coverslip) and BirA (0.4 μg/coverslip) by Lipofectamine 2000 transfection reagent. At 24-48 hours after transfection, the coverslips are transferred to warm saline buffer for 5 min incubation and mounted onto an imaging dish (Warner RC-41LP). In the imaging dish, neurons are incubated in saline buffer containing QDs and casein (~400× dilution for bQDs, and ~80× dilution for sQDs. Stock purchased from Vector labs, SP-5020) for 5 min at 37° C. and washed with 10 ml of saline buffer with 1 μM biotin. Finally 1 ml of saline buffer is added to the imaging dish that is subsequently mounted on the sample stage of the microscope.

Single Molecule Imaging on Coverslips

Coverslip were coated with PEG with 5% biotin. Quantum dots were diluted in PBS to about 1 nM and flow into the channel on coverslip. After 5-10 min, the quantum dots were washed away by PBS. Therefore, individual QDs are immobilized on the coverslip which is imaged later.

Optics and Imaging

Experiments are performed with a Nikon Ti Eclipse microscope with a Nikon APO 100×1.49 objective. The microscope is equipped with the Perfect Focus System, which stabilizes the sample in z-axis. An Agilent laser system MC400B with 4 fiber-coupled lasers (405 nm, 488 nm, 561 nm and 640 nm) is used for illumination. We use Elements software from Nikon for data acquisition. An Andor EMCCD (DU897) is used for recording. For 3D imaging, a cylindrical lens (CVI Melles Griot, SCX-25.4-5000.0-C-425-675) of 10 m focal length is inserted below the rear end of the objective. A motorized stage from ASI with a piezo top plate (ASI PZ-2000FT) is used for x y z position control. For fluorescence imaging, a quadraband dichroic (Chroma, ZT405-488-561-640RPC) is used and band pass emission filter 525/50, 600/50, 710/40, 641/75 is used.

Tracking AMPAR Receptors:

The sample was first examined under bright-field and only coverslips with neurons in good condition are used for experiments. After focusing on the sample, the Perfect Focus System is activated to minimize the sample drift in z direction. The sample were then scanned in GFP channel (488 excitation, 525/50 emission) for transfected cells. An image of the fluorescent cell is taken for reference. To track the QD labeled receptors, 488 nm or 561 nm lasers is used for excitation and an appropriate band-pass filter for collecting the fluorescence. Movies of 600-1000 frames are acquired with 50 ms exposure time.

| | sQD 527 | sQD 615 | sQD 620 | sQD 655 | Invitrogen QD 705 |
|---|---|---|---|---|---|
| Excitation light | 488 nm | 488 nm/ 561 nm | 488 nm/ 561 nm | 488 nm/ 561 nm | 488 nm/ 561 nm |
| Emission filter | Chroma HQ 535/50 m | Chroma ET 600/50 m | Semrock BrightLine 641/75 | Chroma D 655/40 m | Semrock BrightLine 710/40 |

Super-Resolution of Post-Synaptic Density.

After the tracking experiment, the PALM experiment is carried out on the same neurons. PALM was used for super-resolution of post-synaptic density. Post-synaptic protein Homer1 is used as the PSD marker and its C-terminus is fused to photoactivable protein mGeos. A 405 nm laser pulse is used to activate mGeos proteins from dark to green fluorescent state. The sample is then excited with a 488 nm read out laser and emission is collected with a 535/50 band-pass filter. The cycle is repeated for hundreds of times. The z calibration is created using fluorescent beads on a glass surface and applied to both tracking and PALM data.

Data Analysis and Visualization

For the single molecule coverslip test of QDs, individual quantum dots in a 7 by 7 pixel (pixel size is 160 nm) box with the intensity peak in the center is selected. The intensity count in the box is summed To get the averaged intensity for QDs, the program detected all the QDs in a movie which are above a give threshold, and calculate their average intensity over the entire movie.

QuickPalm, an ImageJ plug-in is used for analyzing tracking data and PALM data, and the x y and z coordinates of detected molecules/QDs are extracted from the image for further analysis.

For the tracking data, centroids of the all the QDs are localized in all the frames and a map of all the places QDs visited is obtained. A Matlab code was used to recover the traces of the QDs. And the diffusion coefficient of traces are calculated in Matlab. For the PALM data, proteins in each frame are localized. A modified version of VMD is used for visualizing the synapses and AMPAR traces based on PALM and tracking data.

REFERENCES

1. Lakowicz, J. R. *Principles of Fluorescence Spectroscopy*. (Springer, 2007).
2. Pinaud, F., Clarke, S., Sittner, A. & Dahan, M. Probing cellular events, one quantum dot at a time. *Nat. Methods* 7, 275-285 (2010).
3. Liu, W. et al. Compact Biocompatible Quantum Dots Functionalized for Cellular Imaging. *J. Am. Chem. Soc.* 130, 1274-1284 (2008).
4. Howarth, M. et al. Monovalent, reduced-size quantum dots for imaging receptors on living cells. *Nat. Methods* 5, 397-399 (2008).
5. Zhan, N., Palui, G., Safi, M., Ji, X. & Mattoussi, H. Multidentate Zwitterionic Ligands Provide Compact and Highly Biocompatible Quantum Dots. *J. Am. Chem. Soc.* 135, 13786-13795 (2013).
6. Groc, L. et al. Surface Trafficking of Neurotransmitter Receptor: Comparison between Single-Molecule/Quantum Dot Strategies. *J. Neurosci.* 27, 12433-12437 (2007).

7. Malinow, R. & Malenka, R. C. Ampa Receptor Trafficking and Synaptic Plasticity. *Annu. Rev. Neurosci.* 25, 103-126 (2002).
8. Czöndör, K. et al. Unified quantitative model of AMPA receptor trafficking at synapses. *Proc. Natl. Acad. Sci.* 201109818 (2012). doi:10.1073/pnas.1109818109
9. Liu, W. et al. Compact Biocompatible Quantum Dots via RAFT-Mediated Synthesis of Imidazole-Based Random Copolymer Ligand. *J. Am. Chem. Soc.* 132, 472-483 (2010).
10. Fernig, D. G. & Duchesne, L. Nanoparticle conjugates. US20110165647 (2011).
11. Kairdolf, B. A. et al. Semiconductor Quantum Dots for Bioimaging and Biodiagnostic Applications. *Annu. Rev. Anal. Chem.* 6, 143-162 (2013).
12. Dubois, F., Mahler, B., Dubertret, B., Doris, E. & Mioskowski, C. A Versatile Strategy for Quantum Dot Ligand Exchange. *J. Am. Chem. Soc.* 129, 482-483 (2007).
13. Pong, B.-K., Trout, B. L. & Lee, J.-Y. Modified Ligand-Exchange for Efficient Solubilization of CdSe/ZnS Quantum Dots in Water: A Procedure Guided by Computational Studies. *Langmuir* 24, 5270-5276 (2008).
14. Duchesne, L., Gentili, D., Comes-Franchini, M. & Fernig, D. G. Robust Ligand Shells for Biological Applications of Gold Nanoparticles. *Langmuir* 24, 13572-13580 (2008).
15. Howarth, M., Takao, K., Hayashi, Y. & Ting, A. Y. Targeting quantum dots to surface proteins in living cells with biotin ligase. *Proc. Natl. Acad. Sci. U.S.A.* 102, 7583-7588 (2005).
16. Howarth, M. & Ting, A. Y. Imaging proteins in live mammalian cells with biotin ligase and monovalent streptavidin. *Nat. Protoc.* 3, 534-545 (2008).
17. Chang, H. et al. A unique series of reversibly switchable fluorescent proteins with beneficial properties for various applications. *Proc. Natl. Acad. Sci.* 109, 4455-4460 (2012).
18. Huang, B., Wang, W., Bates, M. & Zhuang, X. Three-Dimensional Super-Resolution Imaging by Stochastic Optical Reconstruction Microscopy. *Science* 319, 810-813 (2008).
19. Yildiz, A. et al. Myosin V Walks Hand-Over-Hand: Single Fluorophore Imaging with 1.5-nm Localization. *Science* 300, 2061-2065 (2003).
20. Betzig, E. et al. Imaging Intracellular Fluorescent Proteins at Nanometer Resolution. *Science* 313, 1642-1645 (2006). 21. Humphrey, W., Dalke, A. & Schulten, K. VMD: visual molecular dynamics. *J. Mol. Graph.* 14, 33-38, 27-28 (1996).

Unless otherwise explained, all technical and scientific terms used herein have the same meaning as commonly understood by one of ordinary skill in the art to which a disclosed disclosure belongs. The singular terms "a," "an," and "the" include plural referents unless context clearly indicates otherwise. Similarly, the word "or" is intended to include "and" unless the context clearly indicates otherwise. All references cited herein are incorporated by reference.

While the present disclosure can take many different forms, for the purpose of promoting an understanding of the principles of the disclosure, reference will now be made to the embodiments illustrated in the drawings and specific language will be used to describe the same. It will nevertheless be understood that no limitation of the scope of the disclosure is thereby intended. Any alterations and further modifications of the described embodiments, and any further applications of the principles of the disclosure as described herein are contemplated as would normally occur to one skilled in the art to which the disclosure relates.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments, exemplary embodiments and optional features, modification and variation of the concepts herein disclosed may be resorted to by those skilled in the art, and that such modifications and variations are considered to be within the scope of this disclosure as defined by the appended aspects. The specific embodiments provided herein are examples of useful embodiments of the present disclosure and it will be apparent to one skilled in the art that the present disclosure may be carried out using a large number of variations of the devices, device components, methods steps set forth in the present description. As will be obvious to one of skill in the art, methods and devices useful for the present methods can include a large number of optional composition and processing elements and steps.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the aspects herein.

All patents and publications mentioned in the specification are indicative of the levels of skill of those skilled in the art to which the disclosure pertains. References cited herein are incorporated by reference herein in their entirety to indicate the state of the art as of their publication or filing date and it is intended that this information can be employed herein, if needed, to exclude specific embodiments that are in the prior art. For example, when compositions of matter are disclosed, it should be understood that compounds known and available in the art prior to Applicant's disclosure, including compounds for which an enabling disclosure is provided in the references cited herein, are not intended to be included in the composition of matter aspects herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the aspect element. As used herein, "consisting essentially of" does not exclude materials or steps that do not materially affect the basic and novel characteristics of the aspect. In each instance herein any of the terms "comprising", "consisting essentially of" and "consisting of" may be replaced with either of the other two terms. The disclosure illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the disclosure without resort to undue experimentation. All art-known functional equivalents, of any such materials and methods are intended to be included in this disclosure. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended aspects.

Although the present disclosure has been described with reference to certain embodiments thereof, other embodiments are possible without departing from the present disclosure. The spirit and scope of the appended aspects should not be limited, therefore, to the description of the preferred embodiments contained herein. All embodiments that come within the meaning of the aspects, either literally or by equivalence, are intended to be embraced therein. Furthermore, the advantages described above are not necessarily the only advantages of the disclosure, and it is not necessarily expected that all of the described advantages will be achieved with every embodiment of the disclosure.

What is claimed is:

1. A method of making water-soluble, stable fluorescent PEGylated alkanethiol-coated quantum dots, the method comprising:
    contacting quantum dots with PEGylated alkanethiol in a non-oxidative, water-immiscible organic reaction solvent under a non-oxidative gas, wherein the reaction solvent is in contact with an aqueous phase, at elevated temperature of 40-80° C. and time sufficient to coat the dots with the PEGylated alkanethiol, wherein resultant water-soluble, stable fluorescent PEGylated alkanethiol-coated dots enter the aqueous phase, wherein the PEGylated alkanethiol is in a mixture of the PEGylated alkanethiol and functionalized PEGylated alkanethiol.

2. The method of claim 1 wherein the elevated temperature is about 60 C and the time is about 4 hours.

3. The method of claim 1 wherein the gas comprises inert gas that is nitrogen.

4. The method of claim 1 wherein the reaction solvent comprises toluene, chlorobenzene, or octane.

5. The method of claim 1 wherein the aqueous phase comprises tetraethylammonium hydroxide (20% wt) in water.

6. The method of claim 1 wherein:
    the elevated temperature is about 60 C and the time is about 4 hours;
    the gas comprises inert gas that is nitrogen;
    the reaction solvent comprises toluene; and
    the aqueous phase comprises tetraethylammonium hydroxide (20% wt) in water.

7. The method of claim 1 wherein the dots comprise a nanocrystal metal core of CdSe, HgCdSe, CdTe, ZnTe, ZnS, CdS or InAs.

8. The method of claim 1 wherein the dots further comprise a shell of ZnS or CdS.

9. The method of claim 1 wherein the coated dots have a diameter less than 10 nm.

10. The method of claim 1 wherein:
    the dots comprise a nanocrystal metal core of CdSe, CdTe, ZnTe, or ZnS;
    the dots further comprise a shell of ZnS or CdS; and
    the coated dots have a diameter less than 10 nm.

11. The method of claim 1 wherein the PEGylated alkanethiol is in a mixture of the PEGylated alkanethiol and functionalized PEGylated alkanethiol, wherein the functionalized PEGylated is 10% or less of the mixture.

12. The method of claim 1 wherein the PEGylated alkanethiol is in a mixture of the PEGylated alkanethiol and functionalized PEGylated alkanethiol, wherein the functionalized PEGylated alkanethiol is carboxyl PEGylated alkanethiol or amine PEGylated alkanethiol.

13. The method of claim 1 wherein the PEGylated alkanethiol is in a mixture of the PEGylated alkanethiol and functionalized PEGylated alkanethiol, wherein the functionalized PEGylated alkanethiol is a corresponding carboxyl PEGylated alkanethiol.

14. The method of claim 1 wherein the PEGylated alkanethiol is in a mixture of the PEGylated alkanethiol and functionalized PEGylated alkanethiol, wherein the functionalized PEGylated alkanethiol is a corresponding carboxyl PEGylated alkanethiol, wherein the mixture is HSC11(EG)4-OH/HSC11(EG)4-COOH (2.5%).

15. The method of claim 1 wherein the functionalized PEGylated alkanethiols of the coated dots are further functionalized with an affinity tag.

16. The method of claim 1 further comprising isolating the coated dots with anion exchange chromatography.

17. The method of claim 1 further comprising washing the aqueous phase containing the coated dots with a water-immiscible organic wash solvent and then isolating the coated dots with anion exchange chromatography.

18. The method of claim 1 further comprising isolating the coated dots and (a) storing the isolated dots in refrigeration for over one month, and/or (b) storing the isolated dots in a mixture comprising at least 50% ethylene glycol.

19. A composition comprising an organic phase comprising quantum dots and PEGylated alkanethiol, at elevated temperature of 40-80° C. under a non-oxidative gas, in contact with an aqueous phase comprising water-soluble, stable fluorescent corresponding PEGylated alkanethiol-coated quantum dots, wherein the PEGylated alkanethiol is in a mixture of the PEGylated alkanethiol and functionalized PEGylated alkanethiol.

20. The composition of claim 19 wherein the coated dots have a diameter less than 10 nm.

* * * * *